United States Patent [19]
Zhang et al.

[11] Patent Number: 5,843,760
[45] Date of Patent: *Dec. 1, 1998

[54] SINGLE ZYMOMONAS MOBILIS STRAIN FOR XYLOSE AND ARABINOSE FERMENTATION

[75] Inventors: Min Zhang, Lakewood; Yat-Chen Chou, Wheat Ridge, both of Colo.; Stephen K. Picataggio, Landenberg, Pa.; Mark Finkelstein, Fort Collins, Colo.

[73] Assignee: Midwest Research Institute, Kansas City, Mich.

[*] Notice: The term of this patent shall not extend beyond the expiration date of Pat. No. 5,726,053.

[21] Appl. No.: 851,767

[22] Filed: May 6, 1997

Related U.S. Application Data

[63] Continuation-in-part of Ser. No. 421,996, Apr. 14, 1995, Pat. No. 5,726,053, which is a continuation-in-part of Ser. No. 228,303, Apr. 15, 1994, Pat. No. 5,514,583.

[51] Int. Cl.$^6$ .............................. C12N 1/21; C12N 15/74; C12P 7/06
[52] U.S. Cl. ..................................... 435/252.3; 435/320.1; 435/243; 435/161; 435/163; 435/165; 435/822; 536/23.2
[58] Field of Search .............................. 435/252.3, 320.1, 435/243, 161, 163, 165, 822; 536/23.2

[56] References Cited

U.S. PATENT DOCUMENTS

| | | | |
|---|---|---|---|
| 4,731,329 | 3/1988 | Lawford | 435/161 |
| 4,812,410 | 3/1989 | Lawford | 435/161 |
| 4,816,399 | 3/1989 | Lawford | 435/161 |
| 4,876,196 | 10/1989 | Salzbrunn | 435/161 |
| 5,000,000 | 3/1991 | Ingram et al. | 435/161 |
| 5,028,539 | 7/1991 | Ingram et al. | 435/161 |
| 5,041,378 | 8/1991 | Drummond et al. | 435/234 |
| 5,168,056 | 12/1992 | Frost | 435/172.3 |
| 5,266,475 | 11/1993 | Lee et al. | 435/234 |
| 5,272,073 | 12/1993 | Frost et al. | 435/155 |

OTHER PUBLICATIONS

M.E. Burnette et al., "Molecular Characterization of the Zymomonas mobilis Enolase (eno) Gene", J. Bacteriol. 174(20): 6548–6553.

G.A. Sprenger, "Approaches to Broaden the Substrate and Product Range of the Ethanologenic Bacterium Zymomonas mobilis by Genetic Engineering", J. Biotechnol. 27(3) 225–237.

S.D. Feldmann et al., "Pentose Metabolism in Zymomonas mobilis Wild–Type and Recombinant Strains", Appl. Microbiol. 38:354–361.

N. Lee et al. "The Organization of the araBAD Operon of Escherichia coli", Gene 47: 231–244, 1986.

Primary Examiner—Rebecca E. Prouty
Attorney, Agent, or Firm—Ken Richardson

[57] ABSTRACT

This invention relates to single microorganisms which normally do not ferment pentose sugars which are genetically altered to ferment the pentose sugars, xylose and arabinose, to produce ethanol, and a fermentation process utilizing the same. Examples include Zymomonas mobilis which has been transformed with a combination of E. coli genes for xylose isomerase, xylulokinase, L-arabinose isomerase, L-ribulokinase, L-ribulose 5-phosphate 4-epimerase, transaldolase and transketolase. Expression of added genes are under the control of Z. mobilis promoters. These newly created microorganisms are useful for fermenting glucose, xylose and arabinose, produced by hydrolysis of hemicellulose and cellulose or starch, to produce ethanol.

10 Claims, 3 Drawing Sheets

SINGLE ZYMOMONAS MOBILIS STRAIN FOR XYLOSE AND ARABINOSE FERMENTATION

This patent application is a continuation-in-part of patent application Ser. No. 08/421,996, filed Apr. 14, 1995, now U.S. Pat. No. 5,726,053, which in turn is a continuation-in-part of patent application Ser. No. 08/228,303, filed Apr. 15, 1994 (now U.S. Pat. No. 5,514,583), both of which are incorporated by reference in their entirety.

CONTRACTUAL ORIGIN OF THE INVENTION

The United States Government has rights in this invention pursuant to Contract No. DE-AC36-83CH10093 between the United States Department of Energy and the Midwest Research Institute.

FIELD OF THE INVENTION

This invention relates to recombinant *Zymomonas mobilis* strains, metabolizing D-xylose and L-arabinose, and bearing xylose and arabinose utilization, and pentose-phosphate pathway genes, useful for the fermentation of the pentoses along with glucose in agricultural and cellulosic biomass to ethanol. This invention also relates to the process of using these strains for rapid and efficient fermentation of the pentose components in agricultural and cellulosic biomass to ethanol.

BACKGROUND OF THE INVENTION

Cellulosic biomass is a favorable feedstock for fuel ethanol production because it is both readily available and less expensive than either corn or sugarcane. However, substantial hurdles must be overcome before a typical cellulosic feedstock can be utilized effectively as a substrate for the fermentative production of ethanol. The typical feedstock is comprised of approximately 35%–45% cellulose, 30–40% hemicellulose, 15% lignin and 10% of other components. The cellulose fraction is comprised of polymers of the hexose sugar, glucose. The hemicellulose fraction is comprised mostly of pentose sugars, and substantially of xylose. Although xylose is the dominant pentose in the hemicellulose fraction the levels of arabinose are significant in some cellulosic feedstocks such as switchgrass or corn fiber. Corn fiber contains approximately 14.8% (w/w) arabinose.

Whereas microorganisms are known that can efficiently ferment the glucose component in cellulose, conversion of the xylose and arabinose in the hemicellulose fraction to ethanol has been difficult and this remains to be one of the economical bottlenecks in the biomass to ethanol conversion scheme. The rapid and efficient utilization of the xylose and arabinose components in cellulosic biomass is desirable in the development of a commercial process.

*Zymomonas mobilis* is a bacterium that has been utilized as a natural fermentative agent in the production of alcoholic beverages, such as pulque and palm wines produced from plant saps. Comparative performance trials have suggested that Zymomonas may become an important industrial ethanol-producing microorganism because of its 5–10% higher yield and up to 5-fold higher productivity compared to traditional yeast fermentations. Because of its potential value, several processes based on the use of Zymomonas for production of industrial ethanol from glucose-based feedstocks have been disclosed in U.S. Pat. Nos. 4,731,329, 4,812,410, 4,816,399, and 4,876,196.

While Zymomonas may become an important fuel ethanol-producing microorganism from glucose-based feedstocks, its substrate utilization range is restricted to fermentation of glucose, sucrose and fructose and, as such, it is not naturally suited for fermentation of the xylose and arabinose components in cellulosic feedstocks. Zymomonas contains the Enter-Douderoff pathway that allows it to ferment glucose very efficiently to ethanol as the sole fermentation product. However, Zymomonas is naturally unable to ferment the xylose and arabinose in cellulosic biomass because it lacks the essential pentose metabolism pathways. Thus, an opportunity exists to genetically engineer this organism for the fermentation of xylose and arabinose to ethanol.

Genetic engineering attempts have been made to enhance ethanol production by fermentation by transferring genes from one species to another. For example, see U.S. Pat. Nos. 5,000,000 and 5,028,539. Gene cloning and expression of various enzymes including enzymes for creating a new metabolic pathway are also known. For example see U.S. Pat. Nos. 5,272,073, 5,041,378, 5,168,056 and 5,226,475. However, none of these discoveries has successfully broadened the fermentable substrate range of a microorganism which could not previously ferment pentose sugars to ethanol.

Previous attempts to introduce a pentose catabolic pathway from either Xanthomonas or Klebsiella into Zymomonas have been unsuccessful and the recombinant strains were incapable of growth on xylose as the sole carbon source (Feldmann et al., 1992, Appl. Microbiol. Biotechnol. 38:354–361; Liu et al., 1988. J. Biotechnol. 7:61–77)

The wild-type *Z. mobilis* ferments only glucose, sucrose and fructose and is not able to utilize pentoses, such as xylose and arabinose. Enzymatic analysis indicated that *Z. mobilis* lacks functional pentose metabolic pathways necessary to ferment xylose and arabinose. We have developed the xylose-fermenting *Z. mobilis* by introduction and expression of four genes encoding xylose-assimilating enzymes, xylose isomerase and xylulokinase as well as pentose-phosphate pathway enzymes, transaldolase and transketolase (Picataggio et al., U.S. Pat. No. 5,514,583). Independently, we have also developed the arabinose-fermenting *Z. mobilis* by introduction of five genes encoding L-arabinose-assimilating enzymes, L-arabinose isomerase, L-ribulokinase and L-ribulose-5-phosphate 4-epimerase as well as the pentose-phosphate pathway enzymes, transaldolase and transketolase (Picataggio et al., U.S. Ser. No 08/421,996).

SUMMARY OF THE INVENTION

The present invention provides a single *Zymomonas mobilis* biocatalyst capable of converting both xylose and arabinose along with glucose to ethanol. Seven genes (xylose isomerase, xylulokinase, L-arabinose isomerase, L-ribulokinase, L-ribulose-5-phosphate 4-epimerase, transketolase, and transaldolase) which encode the enzymes necessary for converting xylose and arabinose to common intermediates of Zymomonas' central glycolytic pathway were simultaneously introduced into Zymomonas under the control of strong promoters that direct their expression, even in the presence of glucose. The newly engineered strain can grow on either xylose, arabinose, or glucose as the sole carbon source and ferment the single sugar or a combination of the sugars directly to ethanol. By introducing the genes encoding xylose isomerase and xylulokinase, L-arabinose isomerase, L-ribulokinase and L-ribulose-5-phosphate 4-epimerase, xylose and arabinose can be converted to xylulose-5-phosphate. Then, by introducing two more genes encoding enzymes in the pentose phosphate pathway, comprising transaldolase and transketolase, xylulose-5-phosphate can be further converted to the key intermediates that couple pentose metabolism to the glycolytic Entner-Douderoff pathway and consequently, permit the microorganism to metabolize xylose and arabinose to ethanol.

A further aspect of the present invention is to enable the Z. mobilis to ferment both xylose and arabinose, by introducing and expressing the genes for both xylose-assimilating enzymes, xylose isomerase and xylulokinase, and arabinose-assimilating enzymes, L-arabinose isomerase, L-ribulokinase and L-ribulose-5-phosphate 4-epimerase, as well as the pentose-phosphate pathway enzymes, transaldolase and transketolase into Z. mobilis. In particular, compositions of Z. mobilis are provided which contain the xylose isomerase and xylulokinase genes from Escherichia coli cloned precisely under the control of the Z. mobilis glyceraldehyde-3-phosphate dehydrogenase (GAP) promoter, and the L-arabinose isomerase, L-ribulokinase and L-ribulose-5-phosphate 4-epimerase genes from Escherichia coli cloned precisely under the control of the Z. mobilis GAP promoter, and transaldolase and transketolase genes from Escherichia coli cloned precisely under the control of the Z. mobilis enolase (ENO) promoter. The cloned genes may be provided on any number of vectors but preferably are contained on a single plasmid vector. More preferably, the genes are integrated into the host genome. All the genes are coordinately expressed in the cells of Z. mobilis, conferring upon said cells the ability to grow on and ferment xylose and/or arabinose directly to ethanol.

Another aspect of the present invention is cultures of microorganisms with the above-described abilities. The cultures may be biologically pure or be mixed with other strains of different organisms to aid in the metabolism of the substrates or a mixture of substrates into ethanol.

Yet another aspect of the invention is a process for producing a newly engineered strain that can grow on and ferment either xylose, arabinose or glucose as the sole carbon source to ethanol.

An additional aspect of the present invention is a process for producing ethanol from the pentoses, xylose and/or arabinose, along with glucose, produced by hydrolysis of hemicellulose and cellulose or starch in agricultural and cellulosic biomass (such as switch grass, wheat straw, corn cobs, corn fiber and spent grains), by culturing the above mentioned genetically-engineered microorganisms in a culture medium containing pentoses.

DESCRIPTION OF THE PREFERRED EMBODIMENTS

Figure 1:
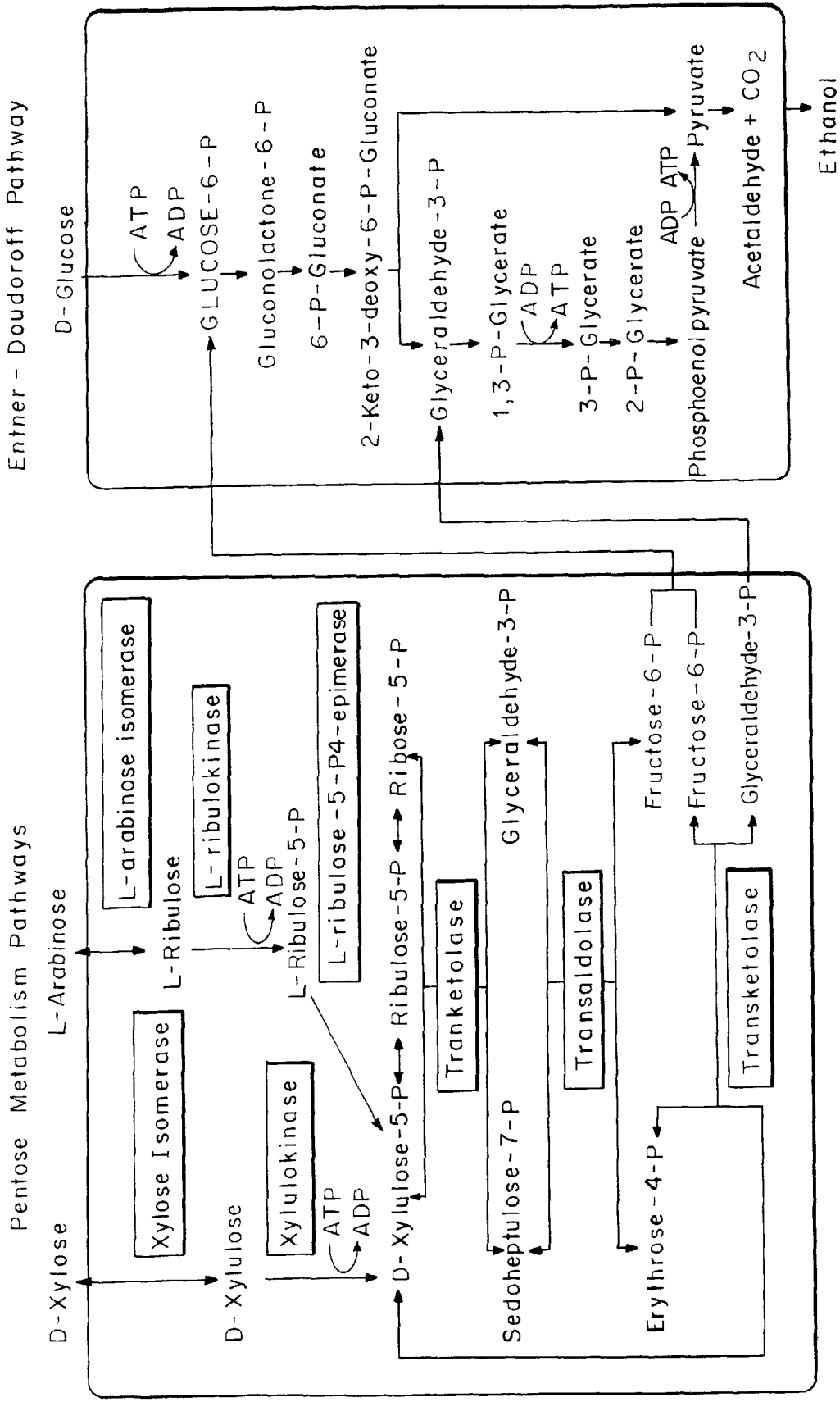
FIG. 1 shows a schematic of a process of enabling Z. mobilis to ferment both xylose and arabinose.

This invention is the development of recombinant Zymomonas strains with an expanded substrate utilization range and which are capable of growth on and/or efficient ethanol production from xylose and/or arabinose, alone or in combination, as the sole carbon source.

The microorganisms used to prepare the present invention are those which are capable of being genetically altered to produce the necessary enzymes to form a metabolic pathway for catabolizing pentose sugars, particularly xylose and arabinose. The microorganism may naturally have some enzymes in the pathway but is not able to ferment xylose or arabinose into ethanol until it has been genetically altered.

The manner of genetic alteration may use any combination of known genetic engineeering techniques such as mutation and addition of foreign DNA, provided that the microorganism is able to ferment pentose sugars to ethanol after treatment. Foreign DNA may be introduced into the microorganism by any conventional technique such as conjugation, transformation, transduction or electroporation.

Many microorganisms which are capable of fermenting sugars to ethanol lack at least one of the genes for the enzymes which make up a metabolic pathway for converting xylose, arabinose and other pentoses into ethanol. Exogenous genes may be added to complete a metabolic pathway. One need not add genes necessary for every step if the host microorganism already produces an enzyme in the pathway. The number of genes to be added will depend on the starting microorganism. In the situation of imparting both xylose and arabinose fermentation capability to naturally occurring Z. mobilis, seven genes may be added or native genes altered to complete the pathway for metabolizing xylose and arabinose to an intermediate which is further metabolized to ethanol using the glycolytic Entner-Douderoff pathway.

The indigenous Zymomonas genes may be altered by any known genetic manipulation technique to provide a protein with the necessary enzyme activity to produce the desired metabolic pathway. The altered genes may complement one or more of the introduced genes from another host to complete the metabolic pathway. The use of this procedure may be advantageous by reducing the number of genes one needs to add to the host cell. For example, Zymomonas's native transketolase may be used to substitute for a foreign transketolase gene, such as the one disclosed from E. coli.

Sufficient genes may be added so that the recipient microorganism may ferment xylose, arabinose, mixtures of xylose and arabinose, or other pentose sugars as the sole carbon source. The microorganism may or may not be able to multiply on xylose. arabinose, or combinations of both xylose and arabinose, as the sole carbon source but may be capable of fermenting xylose, arabinose, or combinations of both xylose and arabinose, to ethanol.

A gene may be added to a cell by way of a vector. The vector may be in the form of a plasmid, cosmid or virus which is compatible to the cell's DNA and any resident plasmids. Generally, vectors either integrate into the recipient microorganism's DNA or the vector has an origin of replication to stably maintain the vector throughout many microbial generations. The origin of replication may code for replication under a wide range of stringency conditions.

To express the gene(s), a structural gene is generally placed downstream from a promotor region on the DNA. The promotor must be recognized by the recipient microorganism. In addition to the promotor, one may include regulatory sequences to either increase expression or to control expression. Expression may be controlled by an inducer or a repressor so that the recipient microorganism expresses the gene(s) only when desired.

In a preferred embodiment of the invention, xylose, arabinose or other pentose metabolic pathway genes are obtained from pentose metabolizing microorganisms and added to Zymomonas which does not otherwise ferment pentose to ethanol. Especially preferred is *Zymomonas mobilis* which historically has been used for fermenting sugar containing liquids (plant sap) into alcoholic beverages. Certain strains of Zymomonas are tolerant of up to 1.5% sodium chloride and other mutants are tolerant to acetic acid, other microbial inhibitors, high temperatures and/or high ethanol concentrations. The selection of host strain will depend on the substrate being used.

In another embodiment of the invention, the source for the genes encoding pentose metabolism is selected from the group consisting of: Xanthomonas, Klebsiella, *E. coli*, Rhodobacter, Flavobacterium, Acetobacter, Gluconobacter, Rhizobium, Agrobacterium, Salmonella, Pseudomonads and Zymomonas. In general the source of the genes for pentose metabolism is any Gram-negative bacterium capable of utilizing pentose sugars for growth. A preferred organism for the source of genes is *E. coli*. The preferred genes encode xylose isomerase, xylulokinase, L-arabinose isomerase, L-ribulokinase, and L-ribulose 5-phosphate 4-epimerase, transaldolase and transketolase. Expression of these genes is under the control of promoters that function in Zymomonas. Strong glycolytic promoters are preferred. The promoters for glyceraldehyde-3-phosphate dehydrogenase and enolase are particularly preferred. Different genes may be under the control of different promoters or other expression altering sequences.

Some or all of the genes may be located together in the same vector or they may be on different vectors or integrated into the genome. Their expression may be such that the newly formed metabolic pathway is formed to enable the microorganism to ferment xylose, arabinose, combinations of both xylose and arabinose or other pentoses, to ethanol. Preferably, the genes for xylose isomerase, xylulokinase, L-arabinose isomerase, L-ribulokinase, L-ribulose 5-phosphate 4-epimerase, transaldolase and transketolase are under the control of one or more functional promoters when in Zymomonas. The genes on a vector may be in any order, grouping or orientation relative to each other, providing that, if more than one promotor is present on the vector, the direction of transcription from one promotor does not adversely affect expression of the genes.

Most preferably, in the embodiments of the present invention, a genetic element comprising any two or more of the above described genes may be placed on the same vector. Particularly preferred is a plasmid containing both the transaldolase and the transketolase genes. These vectors preferably have the genes under the control of a promotor recognized by Zymomonas. The Examples below show pZB301, pZB401, pZB402 and 403, all of which are examples of vectors carrying DNA encoding two or more of the above described genes.

The expression of the genes and the resulting functional activity of their corresponding gene products represent a new biochemical pathway that links pentose metabolism to the central Entner-Douderoff pathway in Zymomonas, conferring upon these cells the ability to grow on and ferment xylose, arabinose or combinations of both xylose and arabinose directly to ethanol. The genes on a vector may be in any orientation relative to the direction of transcription of these genes provided that they do not interfere with each other. The examples below have shown that the genes perform in essentially the same way regardless of orientation.

The microorganism according to the present invention may be mixed with xylose, arabinose, combinations of both xylose and arabinose or other pentose contained in a medium to produce ethanol. The medium may include other fermentable sugars, such as glucose. The range of percentage with individual sugar in a mixture contianing glucose, xylose and arabinose may vary from substrate to substrate. It is reasonable to expect that the microorganism according to the present invention can ferment a mixture of up to about 16% sugar to ethanol. If microbial growth is desired, other nutrients which are necessary for microbial growth may be added and the microorganism allowed to reproduce.

Transaldolase and transketolase are key enzymes of the pentose phosphate pathway and are required for fermentation by Zymomonas of any pentose sugar which can be converted to xylulose-5-phosphate to ethanol. A preferred embodiment is the expression of these genes in Zymomonas in conjunction with any other sets of genes that allow the utilization of pentose sugars, such as xylose and arabinose. An example of added genes needed for fermentation of xylose and arabinose are xylose isomerase, xylulokinase, L-arabinose isomerase, L-ribulokinase, and L-ribulose 5-phosphate 4-epimerase genes in addition to transaldolase and transketolase genes.

In an especially preferred embodiment of the invention, genes for xylose, arabinose and other pentose utilization, and genes for transaldolase and transketolase are obtained from organisms containing them, and are expressed in Zymomonas. Efficient transport of the pentoses into Zymomonas may be through native Zymomonas transport proteins, mutated Zymomonas transport proteins, or through the addition of new facilitated transporters introduced by cloning new transport genes into Zymomonas with or without mutagenesis of the cloned transport genes.

The step of microbial growth may be separate from fermentation. Xylose, arabinose and other pentoses, or mixtures thereof may be used as a carbon source for microbial growth or one can separately culture the microorganism on any medium (with or without a pentose) until sufficient numbers of microorganisms are present as a first step and then a pentose containing medium is added for fermentation in a second step. If a two step method is used, one may control expression of the genes in the new metabolic pathway so that greater expression occurs during the second step.

The choice of substrates will depend on cost and supply of the substrate to be fermented to ethanol. A typical low-cost supply of pentoses is from hemicellulose. Xylose, arabinose and other pentoses are liberated from hemicellulosic materials by steam and/or an acid or alkali. Smaller amounts of other sugars such as glucose are also separated during this treatment and are also fermented by Zymomonas to ethanol.

When the substrate is cellulosic material, the cellulose may be hydrolyzed to sugars simultaneously or separately and also fermented to ethanol. Since hemicellulose is generally easier to hydrolyze to sugars than cellulose, it is preferable to prehydrolyze the cellulosic material, separate the pentoses and then hydrolyze the cellulose by treatment with steam, acid, alkali, cellulases or combinations thereof to form glucose. Starch-hydrolysing enzymes may be added to release glucose from residual starch in argricultural residues. Hexoses and pentoses may be fermented to ethanol simultaneously, sequentially, separately or together using the microorganism of the present invention. If desired, the hexoses may be fermented to ethanol by a different microorganism than the pentoses, such as yeast, natural Zymomonas, etc.

Many fermentation conditions are known per se as shown by the references mentioned in the Background of the Invention section. *Zymomonas mobilis* is a facultative anaerobic bacterium. It has theoretical yields of ethanol from sugar of up to 97% which provides for little microbial growth, if desired. The optimum pH conditions range from about 3.5 to about 7.5. Substrate concentrations of up to about 25% (based on glucose), and under some conditions even higher, may be used. Unlike other ethanol producing microorganisms, no oxygen is needed at any stage for microorganism survival. Also unlike yeast, oxygen does not drastically reduce ethanol productivity or greatly increase cell growth. Agitation is not necessary but may enhance availability of substrate and diffusion of ethanol. Accordingly, the range of fermentation conditions may be quite broad. Likewise, any of the many known types of apparatus may be used for the present invention.

The microorganism according to the present invention may be used as a biologically pure culture or it may be used with other ethanol producing microorganisms in mixed culture. Microorganisms able to ferment xylose and arabinose can be cultured itself or cultured and then mixed with other microorganisms able to ferment glucose. Biologically pure cultures are generally easier to optimize but mixed cultures may be able to utilize additional substrates. One may also add enzyme(s) to the fermenter to aid in the degradation of substrates or to enhance ethanol production. For example, cellulase may be added to degrade cellulose to glucose simultaneously with the fermentation of glucose to ethanol by microorganisms in the same fermenter. Likewise, a hemicellulase may be added to degrade hemicellulose.

In the preferred embodiment using a genetically engineered Zymomonas, cultures are found to be relatively resistant to contamination by other microorganisms. Nonetheless, it is preferred to eliminate or disable preexisting deleterious microorganisms in the substrate added to the Zymomonas culture.

After fermentation, the ethanol, which may achieve concentrations of up to about 13%, is separated from the fermentation broth by any of the many conventional techniques known to separate ethanol from aqueous solutions. These methods include evaporation, distillation, solvent extraction and membrane separation. Particles of substrate or microorganisms may be removed before ethanol separation to enhance separation efficiency.

Once the fermentation is complete, excess microorganisms and unfermented substrate may be either recycled or removed in whole or in part. If removed, the microorganisms may be killed, dried or otherwise treated. This mixture may be used as animal feed, fertilizer, burnt as fuel or discarded.

While the discussion of the fermentation in this specification generally refers to a batch process, parts or all of the entire process may be performed continuously. To retain the microorganisms in the fermenter, one may separate solid particles from the fluids. This may be performed by centrifugation, flocculation, sedimentation, filtration, etc. Alternatively, the microorganisms may be immobilized for retention in the fermenter or to provide easier separation.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples, which are offered by way of illustration and not by way of limitation.

EXAMPLE I

Expression of Xylose and Arabinose Metabolism, and Pentose Phosphate Pathway Genes in *Z. mobilis*

Plasmids were constructed containing all seven genes, xylose isomerase, xylulokinase, L-arabinose isomerase, L-ribulokinase, L-ribulose-5-phosphate 4-epimerase, transaldolase and transketolase under control of strong, constitutive *Z. mobilis* promoters that allow high expression of all the genes and transformed *Z. mobilis*. Specifically, xylose isomerase and xylulokinase are controlled under the *Z. mobilis* glyceraldehyde-3-phosphate dehydrogenase (GAP) promotor in a $P_{gap}$-xy1Axy1B operon; L-arabinose isomerase, L-ribulokinase and L-ribulose-5-phosphate 4-epimerase are also controlled under the *Z. mobilis* GAP promotor in a $P_{gap}$-araBAD operon; transaldolase and transketolase are controlled under the *Z. mobilis* enolase (ENO) promotor in a $P_{eno}$-tal/tkt operon.

EXAMPLE II

Preparation of A Single Plasmid containing Xylose and Arabinose[-Fermentating Capability] Metabolism, and Pentose Phosphate Pathway Genes Based on pZB4

To contruct a single plasmid containing xylose and arabinose metabolism, and pentose phosphate pathway genes which includes xylose isomerase, xylulokinase, L-arabinose isomerase, L-ribulokinase, L-ribulose-5-phosphate-4-epimerase, transaldolase and transketolase, the xylose plasmid pZB4 (Picataggio et al., U.S. Pat. No. 5,514,583) was partially digested with NotI followed by ligation with a gel purified 4.4-kb NotI fragment containing $P_{gap}$-araBAD operon from pZB206 (Picataggio et al., U.S. Ser. No. 08/421,996). The ligation mixture was used to electroporate *E. cold* B/r araA⁻ and cells were plated on MacConkey plates containing L-arabinose and tetracycline (Tc).

Figures 2A, 2B:
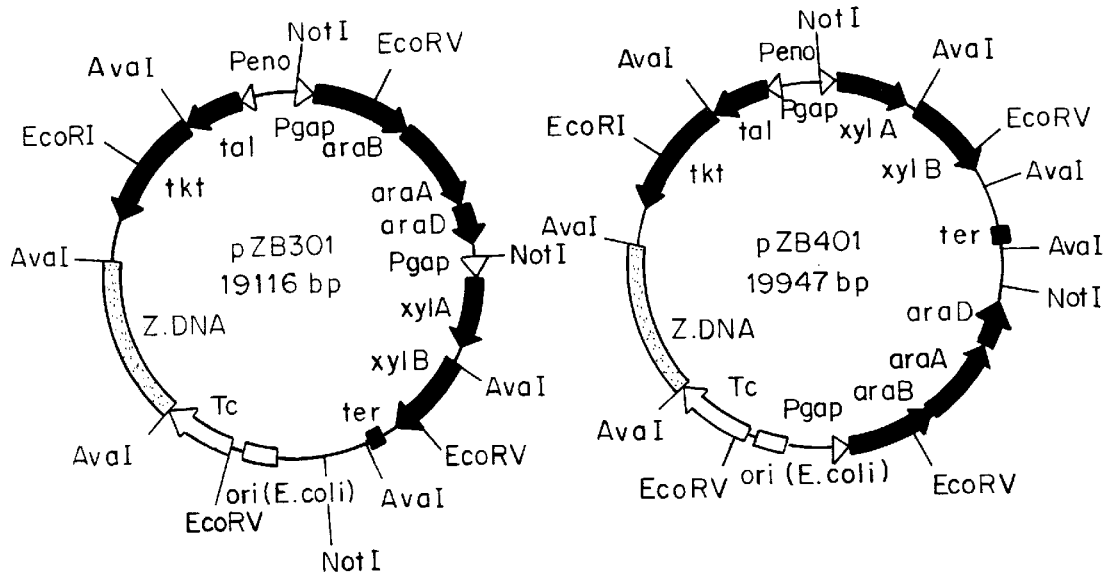
FIG. 2 depicts the plasmid maps of pZB301, pZB401, pZB402, and pZB403.
Figures 2C, 2D:
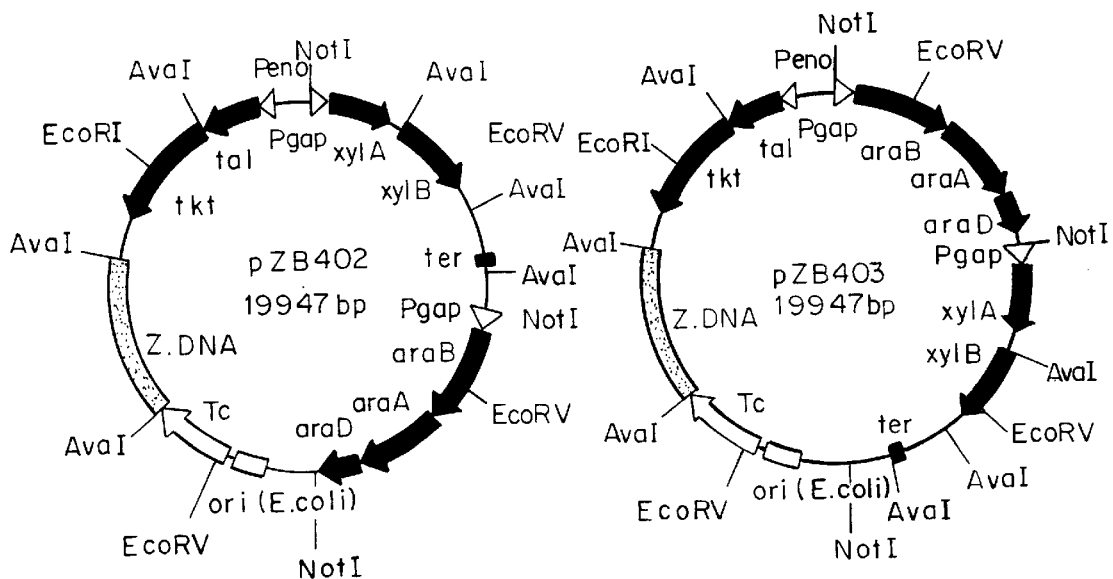

The Ara⁺Tcʳ transformants were examined for the presence of the correct $P_{gap}$-araBAD operon insert in pZB4. DNA analysis of transformants indicated that NotI insert containing $P_{gap}$-araBAD operon was inserted clockwise in the NotI site upstream to $P_{gap}$-xy1/Axy1B operon. The resulting plasmid, is designated as pZB301 (FIG. 2).

EXAMPLE III

Preparation of Single Plasmids Containing Xylose and Arabinose Metabolism, and Pentose Phosphate Pathway Genes Based on pZB4L Efforts were also made to construct single plasmid containing xylose and arabinose metabolism, and pentose phosphate pathway genes based on another xylose plasmid pZB4L. Similarly, pZB4L was digested with NotI followed by ligation with a gel purified 4.4-kb NotI fragment containing $P_{gap}$-araBAD operon from pZB206. *E. coli* HB101 was electroporated with the ligation mixture followed by selection on MacConkey plates containing L-arabinose and tetracycline (Tc). The Ara⁺Tcʳ transformants were examined for the presence of the correct $P_{gap}$-araBAD operon insert in pZB4L. DNA analysis indicated three types of orientations of the insert. These plasmids were designated as pZB401, pZB402, and pZB403 (FIG. 2).

EXAMPLE IV

Transfer Xylose and Arabinose Metabolism, and Pentose Phosphate Pathway Genes into *Zymomonas mobilis*

The arabinose-fermenting strain *Z. mobilis* 39676 (pZB206) cured of the plasmid pZB206 was designated as *Z. mobilis* 206C. *Z. mobilis* 206C is used as the host for transformation.

Plasmids pZB301, pZB401, pZB402 and pZB403 prepared above were separately transformed into Z. mobilis 206C by electroporation of approximately $10^9$ cells/ml with 2 μg DNA in 40 μl of 10% (w/v) glycerol at 16 kv/cm, 200 Ω and 25 F. After electroporation, the cells were allowed to recover at 30° C. for 3–16 hours in a liquid medium comprised of 5% glucose, 10% yeast extract (Difco), 5% Tryptone (Difco), 0.25% ammonium sulfate, 0.02% potassium phosphate, dibasic and 1 mM magnesium sulfate. Transformants containing pZB301, pZB401, pZB402 and pZB403 were isolated following anaerobic incubation at 30° C. for 2 or more days in the same medium additionally containing 1.5% agar and tetracycline (20 μg/ml) and were subsequently confirmed by restriction analyses of the plasmid DNA from tetracycline-resistant transformants.

Enzymatic analyses of Z. mobilis 206C (pZB301) and Z. mobilis 206C (pZB401) demonstrated that all seven enzymes are highly expressed as compared to the control strain containing vector pZB186 (Table 1). Z. mobilis 206C strains transformed with pZB301, pZB401, pZ402 or pZB403 were able on media containing either arabinose or xylose as a sole carbon source.

TABLE 1

Summary of Enzymatic Assays

| Strains[1] | Specific Enzyme Activity (U/Mg protein) | | | | | | |
|---|---|---|---|---|---|---|---|
| | XI | XK | L-AI | L-RK | L-Repi | TKT | TAL |
| 206C(pZB186) | 0.03 | 0.08 | nd[2] | 0.58 | 0.01 | 0.01 | 0.07 |
| 206C(pZB301) | 0.29 | 3.30 | 3.25 | 1.34 | 0.22 | 0.55 | 2.04 |
| 206C(pZB401) | 0.25 | 0.82 | 2.22 | 1.56 | 0.29 | 0.57 | 2.25 |

[1]Cells were collected at $OD_{600} = 1.2$.
[2]nd = not detected

EXAMPLE V

Fermentation Performance of Recombinant Zymomonas Containing Xylose and Arabinose Metabolism, and Pentose Phosphate Pathway Genes The fermentation performance of the recombinant Zymomonas containing the xylose isomerase, xylulokinase, L-arabinose isomerase, L-ribulokinase, L-ribulose 5-phosphate 4-epimerase, transaldolase and transketolase genes was evaluated in a medium comprised of 1% (w/v) yeast extract (Difco), 0.2% potassium phosphate, dibasic and either 2% glucose, or 2% xylose, or 2% arabinose, or 2% xylose and 2% arabinose, or 1% glucose and 2% xylose and 2% arabinose.

The recombinant Zymomonas strains were first propagated at 30° C. in the above medium containing 2% glucose, 1% xylose and 1% arabinose in a bottle with 75 ml of working volume without agitation until late log-phase. The cells were then inoculated into 200 ml of the above fermentation medium in a 100 ml bottle at an initial $OD_{600}=$ 0.3–0.4. The cultures were grown at 30° C. under anaerobic conditions staticly without pH control. The cell growth was monitored as optical density at 600 nm. The residual sugars as well as ethanol concentrations were determined on HPLC (HP 1090L, Hewlett Packard, Wilmington, Del.) using a Bio-Rad Aminex HPX-97H column.

Figure 3:
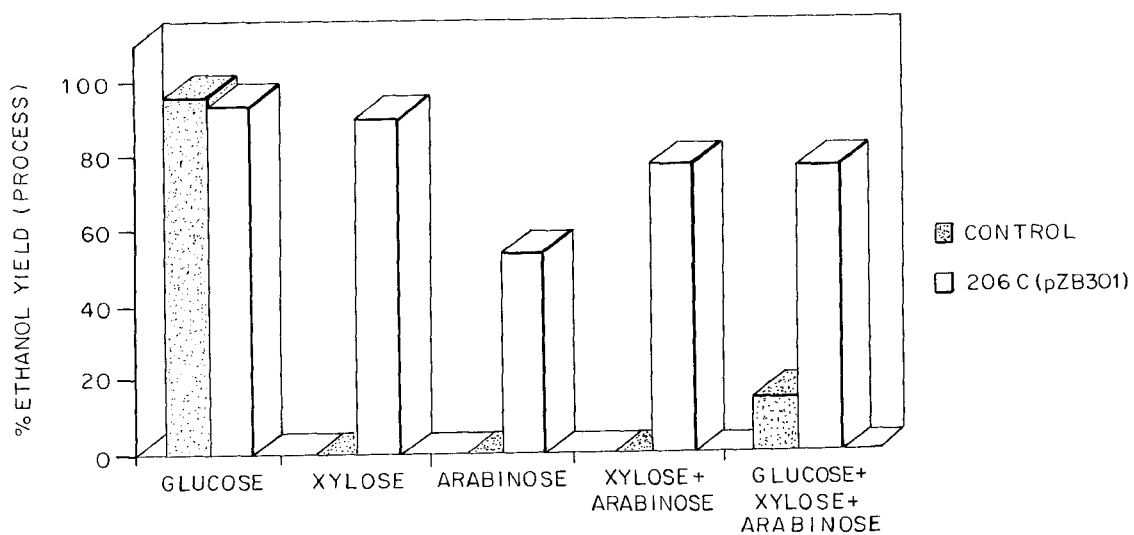
FIG. 3 shows the ethanol yields using a control Zymomonas mobilis and the present recombinant strain when grown on certain sugars or a mixture of certain sugars as the carbon source.

The results presented in FIG. 3 show that in contrast to the control strain containing the shuttle vector alone (206C [pZB186]), the recombinant strain containing the added xylose isomerase, xylulokinase, L-arabinose isomerase, L-ribulokinase, L-ribulose 5-phosphate 4-epimerase, transaldolase and transketolase genes demonstrated growth on and ethanol production from xylose and arabinose, alone or in a combination as a carbon source. The recombinant strain produces ethanol from glucose as efficiently as the control strain at 94% of theoretical yield. The recombinant strain additionally produces ethanol from xylose, or arabinose, or xylose and arabinose at process yields of 91%, 55%, and 79% yield in 96 hours (47 hours for xylose only), respectively. Furthermore, in the presence of glucose and xylose and arabinose, the recombinant strain ferments all three sugars to ethanol at a process yield of 79% yield within 48 hours, thus providing the foundation for advanced process designs with cofermentation of mixed-sugar feedstocks. The recombinant strain produces ethanol from 2% xylose, 2% arabinose, 2% xylose and 2% arabinose, or 1% glucose, 2% xylose and 2% arabinose at 92%, 88%, 94% or 90% of theoretical consumed sugar yield, respectively. The control strain neither grew on nor produced ethanol from xylose, arabinose or xylose and arabinose.

We claim:

1. A microorganism of the genus Zymomonas containing exogenous genes encoding xylose isomerase, xylulokinase, L-arabinose isomerase, L-ribulokinase, L-ribulose-5-phosphate 4-epimerase, transaldolase and transketolase and further comprising at least one promoter recognized by Zymomonas which regulates the expression of at least one of said genes, wherein said microorganism is capable of growing on arabinose and/or xylose, alone or in combination, as the carbon source and fermenting said arabinose and xylose to ethanol, wherein said microorganism without said genes is incapable of growing on or fermenting said arabinose and xylose to ethanol.

2. A microorganism according to claim 1, wherein the genes encoding xylose isomerase, xylulokinase, L-arabinose isomerase, L-ribulokinase, and L-ribulose 5-phosphate 4-epimerase, transaldolase and transketolase were obtained from bacteria selected from the group consisting of Xanthomonas, Klebsiella, E. coli, Rhodobacter, Flavobacterium, Acetobacter, Gluconobacter, Rhizobium, Agrobacterium, Salmonella and Pseudomonads.

3. A microorganism according to claim 1, wherein the genes are integrated into the host genome.

4. A microorganism according to claim 1, wherein said genes are contained on a vector.

5. A microorganism according to claim 4, wherein said xylose isomerase and xylulokinase are expressed under the control of a glyceraldehyde-3-phosphate dehydrogenase promoter in a $P_{gap}$-xyl1A xyl1B operon recognized by Zymomonas; L-arabinose isomerase, L-ribulokinase and L-ribulose-5-phosphate 4-epimerase are also expressed under the control of a glyceraldehyde-3-phosphate dehydrogenase promoter in a $P_{gap}$-araBAD operon recognized by Zymomonas; and transaldolase and transketolase are expressed under the control of an enolase promoter in a $P_{eno}$-tal/tkt operon recognized by Zymomonas.

6. A vector comprising genes encoding xylose isomerase, xylulokinase, L-arabinose isomerase, L-ribulokinase, L-ribulose-5-phosphate 4-epimerase, transaldolase and transketolase and at least one promoter recognized by Zymomonas which regulates expression of said genes.

7. A vector according to claim 6, wherein the enzymes xylose isomerase and xylulokinase are regulated by a glyceraldehyde-3-phosphate dehydrogenase promotor in a $P_{gap}$-xyl1A xyl1B operon recognized by Zymomonas.

8. A vector according to claim 6, wherein the genes encoding L-arabinose isomerase, L-ribulokinase and L-ribulose-5-phosphate 4-epimerase are regulated by a glyceraldehyde-3-phosphate dehydrogenase promoter in a $P_{gap}$-araBAD operon recognized by Zymomonas.

9. A vector according to claim 6, wherein the genes encoding transaldolase and transketolase are regulated by an enolase promoter in a $P_{eno}$-tal/tkt operon recognized by Zymomonas.

10. A microorganism according to claim 2, wherein the genes encoding xylose isomerase, xylulokinase, L-arabinose isomerase, L-ribulokinase, L-ribulose-5-phosphate-4-epimerase, transaldolase and transketolase are obtained from E. coli.

* * * * *

UNITED STATES PATENT AND TRADEMARK OFFICE
CERTIFICATE OF CORRECTION

PATENT NO. : 5,843,760
DATED : December 1, 1998
INVENTOR(S) : Min Zhang et al.

It is certified that error appears in the above-identified patent and that said Letters Patent is hereby corrected as shown below:

On title page, item [73]

In the Assignee:

In line 2, change "Mich." to --Mo.--.

Signed and Sealed this

Thirtieth Day of March, 1999

Attest:

Q. TODD DICKINSON

Attesting Officer     Acting Commissioner of Patents and Trademarks